Figure 1:
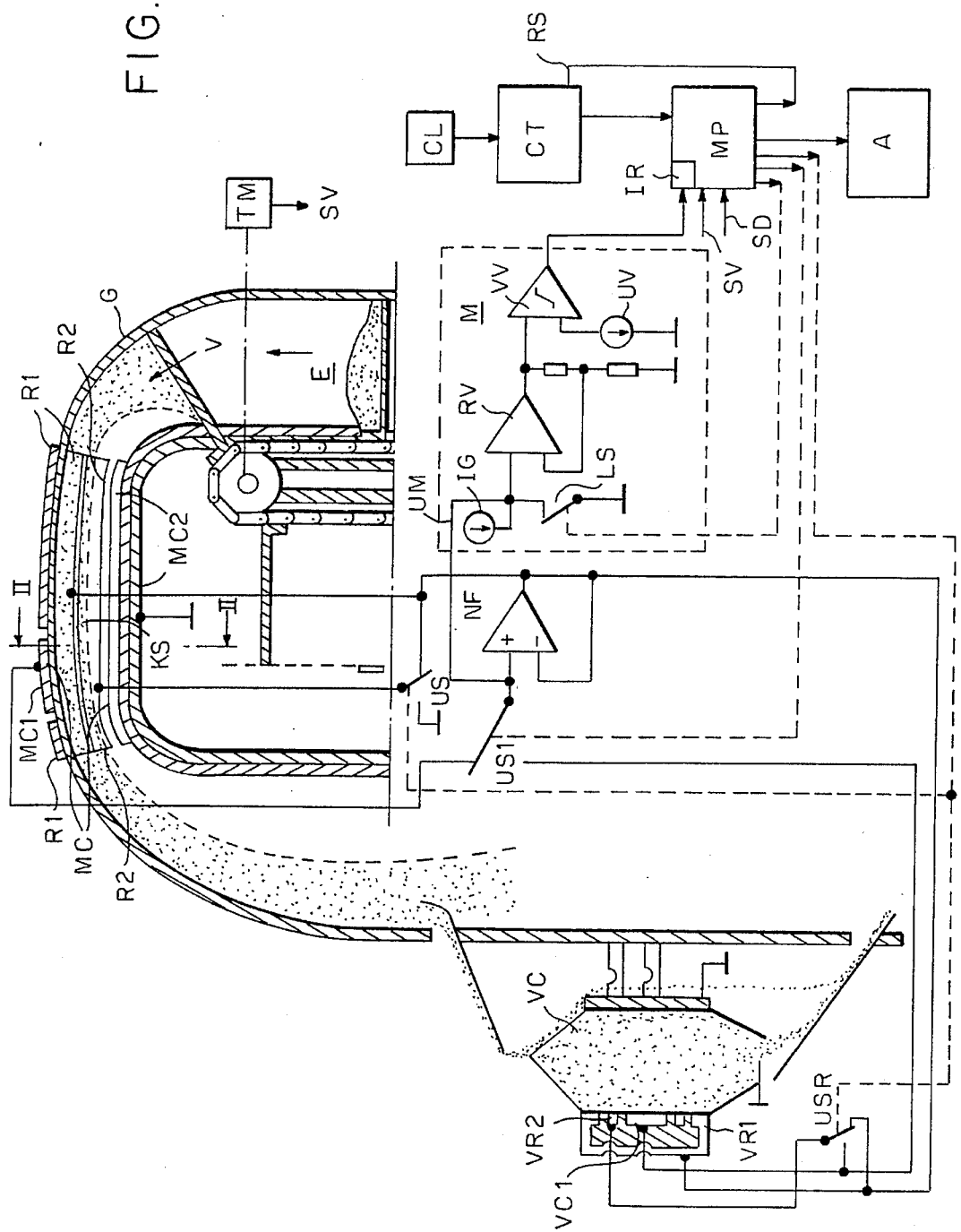

United States Patent [19]

Böttinger et al.

[11] Patent Number: 5,560,246
[45] Date of Patent: Oct. 1, 1996

[54] MASS FLOW RATE MEASURING DEVICE WITH DUAL ELECTRODES

[75] Inventors: Stefan Böttinger, Bielefeld; Horst Weigelt, Gütersloh; Klaus Horn, Brunswick; Weiping Yang, Duisburg, all of Germany

[73] Assignee: Claas Ohg Beschrankt Haftende Offene Handelsgesellschaft, Harsewinkel, Germany

[21] Appl. No.: 387,835

[22] PCT Filed: Aug. 17, 1993

[86] PCT No.: PCT/EP93/02185

§ 371 Date: Feb. 22, 1995

§ 102(e) Date: Feb. 22, 1995

[87] PCT Pub. No.: WO94/04019

PCT Pub. Date: Mar. 3, 1994

[30] Foreign Application Priority Data

Aug. 22, 1992 [DE] Germany .......................... 42 27 922.4
Jun. 3, 1993 [DE] Germany .......................... 43 18 477.4

[51] Int. Cl.[6] .................. G01F 1/58; G01F 1/56; G01F 1/60
[52] U.S. Cl. .................. 73/861.15; 73/861.08; 73/861.73
[58] Field of Search .................. 342/686, 688; 73/861, 861.12, 861.15, 861.08, 861.41, 861.73, 861.05

[56] References Cited

U.S. PATENT DOCUMENTS

| | | | |
|---|---|---|---|
| 4,930,356 | 6/1990 | Proges | 73/861.08 |
| 5,343,761 | 9/1994 | Myers | 73/861.73 |
| 5,351,558 | 10/1994 | Horn et al. | 73/861.08 |
| 5,431,883 | 7/1995 | Barraud | 73/25.05 |

FOREIGN PATENT DOCUMENTS

| | | |
|---|---|---|
| 1942773 | 3/1971 | Germany . |
| 4105857 | 8/1992 | Germany . |
| 8500087 | 1/1985 | WIPO . |

*Primary Examiner*—Richard Chilcot
*Assistant Examiner*—Max Noori
*Attorney, Agent, or Firm*—Browdy and Neimark

[57] ABSTRACT

The invention relates to the type of device for measuring a mass flow in a harvester, where the flow is deflected at the outlet of an elevator (E) at a conveyor shaft wall (G) to form a stratified homogeneous flow and the flow is continuously measured as a function of the fill level by a capacitor (MC). The capacitor has a first capacitor plate (MC1) at a mass flow front side and a second capacitor plate (MC2) at a distance from the mass flow. The first capacitor plate is bordered and enclosed by a first protective electrode (R1) held at the same potential as the first capacitor plate by an impedance transformer. The second capacitor plate includes a portion of the conveyor shaft wall located opposite the first capacitor plate (MC1) and by lateral areas of the conveyor shaft wall. The invention improves this type of device by adding to the first protective electrode at least one partial second protective electrode (R2), where the first protective electrode (R1) extends at least partially perpendicular to the front side on the side walls of the conveyor shaft between the two capacitor plates (MC1, MC2) over at least a partial height (h1, h2) of the mass flow.

18 Claims, 4 Drawing Sheets

MASS FLOW RATE MEASURING DEVICE WITH DUAL ELECTRODES

The invention relates to a device for measuring a mass flow which is deflected at the outlet of an elevator at a conveyor shaft wall, in particular of a harvester, so that it forms a stratified dielectric with a homogeneous speed in a flow rate measuring capacitor disposed there. The first capacitor plate of the flow rate measuring capacitor is disposed at the mass flow side, the second capacitor plate is disposed at a distance from the mass flow. In the process the first capacitor plate is bordered by a protective electrode which is kept at the same potential with the enclosed capacitor plate by means of an impedance transformer. The second capacitor plate is formed by a conveyor shaft wall located opposite the first capacitor plate and by lateral areas of the conveyor shaft.

The mass flow is guided through the flow rate measuring capacitor in such a way that it forms a stratified dielectric with an approximately homogeneous velocity distribution and is passed through a second measuring capacitor which is always completely filled. The two capacitances of these capacitors are detected by means of the same measuring device in order to form a capacitance proportion.

The continuous absolute value measurement of a grain flow in harvesters results in considerable advantages when employing the measured value for controlling and monitoring the operation of the machine, in particular the feed speed, the sifter drives and the cutting height. Further than that, it also permits the preparation of a harvest register which is a basis for soil treatment and fertilization extending over years and adapted to the respective soil and harvest values.

A device of this type is the subject of German Patent Application P 41 05 857 A1.

The measuring device is disposed in the harvester behind the grain elevator, for example a power shovel, in a path bend wherein the mixing of the grain, which is ejected from different path radii and which in the process has different velocities, takes place, wherein the centrifugal force occurring at the bent wall causes packing of the grain and velocity homogenization. The smooth guide path and the evened-out flow of the grain precludes damage of the delicate harvested material.

Different circuit arrangements are suitable for the capacitance comparison measurement, wherein advantageously always the same measuring device is used for measuring both capacitances, so that systematic errors cancel each other out to a large degree.

A first suitable measuring arrangement is distinguished by a carrier frequency measuring bridge, whose input is alternately switched to the two capacitances to be measured and whose associated measured results are compared in a computer.

A further circuit arrangement consists in that the two capacitances to be measured are switched into a carrier bridge as bridge members, so that the bridge output signal is a value for determining the capacitance proportion.

Another type of capacitance proportion measuring takes place in a circuit, in which a capacitance charge of the capacitors by means of a current source is alternatingly performed up to a comparison voltage, wherein the respectively required charge times of the two measuring capacitors are measured, which then must be compared.

A further circuit arrangement, wherein the two capacitances to be compared are disposed in the branches of a bridge circuit, results in a particularly rapid and accurate measurement. In the process an immediate proportion formation takes place, which must then be reduced in accordance with the known functional connection of the bridge circuit to the capacitance proportion, which takes place in a simple calculation by means of equations or association in a table. This functional transformation can be combined with the functional linkage, required anyway, of the capacitance proportion with the function of the stratified dielectric, so that respectively only a mutual processing of a measured result by means of an access to a table or a function calculation is required.

In an embodiment of the bridge measuring circuit containing both measuring capacitors in one measuring branch, the former is provided with an alternating bridge voltage which changes polarity at the time when respectively an upper or a lower predetermined tolerance point of the bridge balance has been reached, wherein the respective times of the two switched polarities are measured and are then placed in a proportion from which the bridge relationship results.

In order to achieve measured results as accurately as possible, in all the above embodiments of the measuring arrangements one of the measuring electrodes of each measuring capacitor is enclosed in a protective electrode which electronically tracks the potential of the measuring electrode. It is intended by means of the protective electrode to assure that an approximately parallel course of the lines of electric flux is provided in the measuring field; only then is there a clear functional relationship between the layer height of the dielectric to be measured and the capacitance. This relationship is used for the conversion of the originally obtained respective proportional value. In the arrangement of the protective electrodes mentioned in the beginning, the required linearity of the lines of electric flux is only assured with a comparatively low mass flow height.

Furthermore, in the device mentioned at the beginning, the position of the measuring electrodes in relation to the area of the optimum layer formation represents a compromise, since specifically light and specifically heavy grains have different trajectories. Grain flows of relatively dry or relatively moist grains occur in such a measuring device, based on the weather. Grains with more moisture have a different trajectory than dry grain of the same type since it has a different coefficient of friction, which has an effect on the deflection. Furthermore, with moist grain a water film is formed which extends over the capacitor plate and the protective electrode. Because of this water film, interfering leakage currents flow between the electrodes. The capacitance measurement is distorted by this ohmic conductor portion.

In the device described in German Patent Application P 41 05 857 A1 the surfaces of the measuring electrodes and of the protective electrodes are provided with an insulating coating for avoiding such leak currents. However, with this coating the wear of the insulating coating by friction—caused by the grain flow—constitutes a large problem. Further than that, in the course of the flow-through of dry grain interfering static charges also occur because of the friction between the grain and the insulating coating.

It is the object of the invention to improve the device for the capacitive measurement of a mass flow, particularly of grain, in such a way that along with a relatively simple construction it has a high degree of measuring accuracy even at large through-puts and with moist grain flows.

The attainment of the object consists in that, in addition to the protective electrode (R1), at least one further partial electrode (R2) is provided and that the protective electrode (R1) extends at least partially on the side walls of the conveyor shaft between the two capacitor plates (MC1, MC2).

Advantageous embodiments are recited in the dependent claims.

Figure 2:
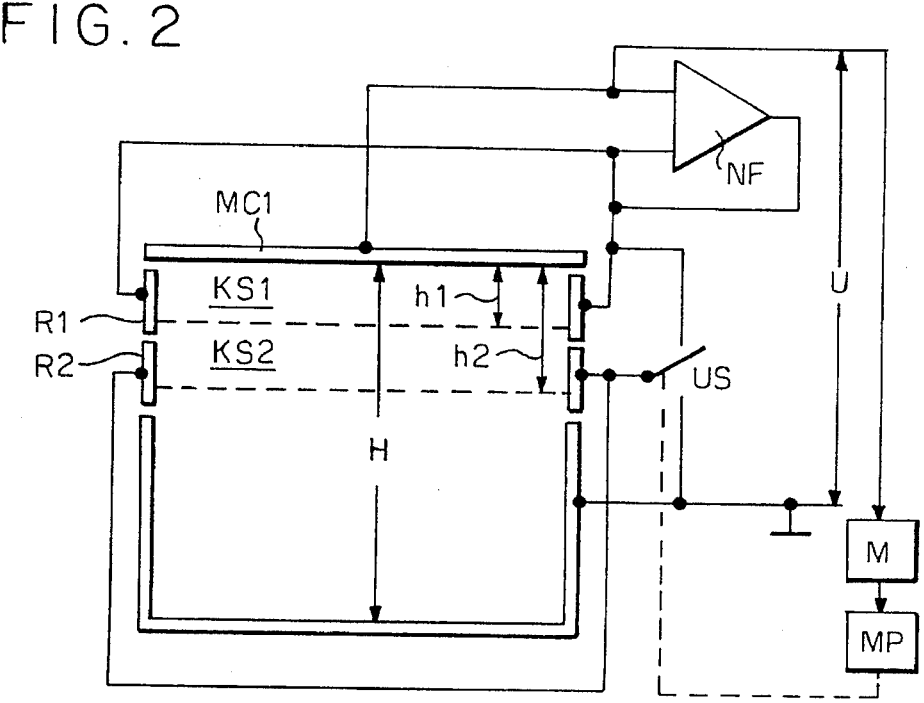
Figure 3:
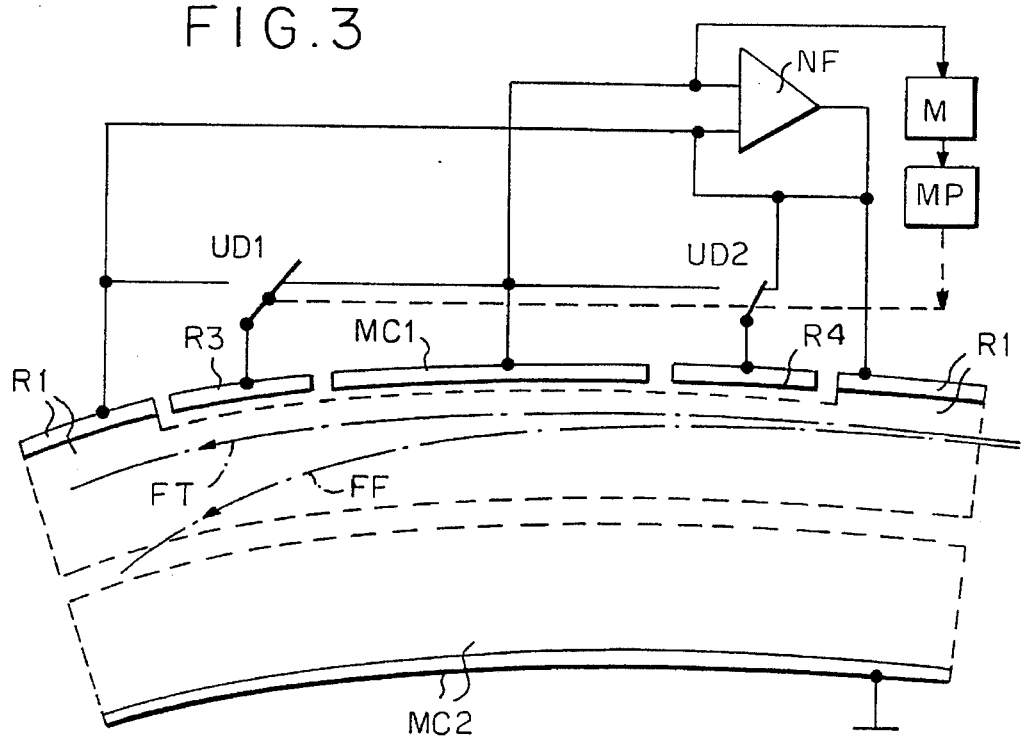
Figure 4:
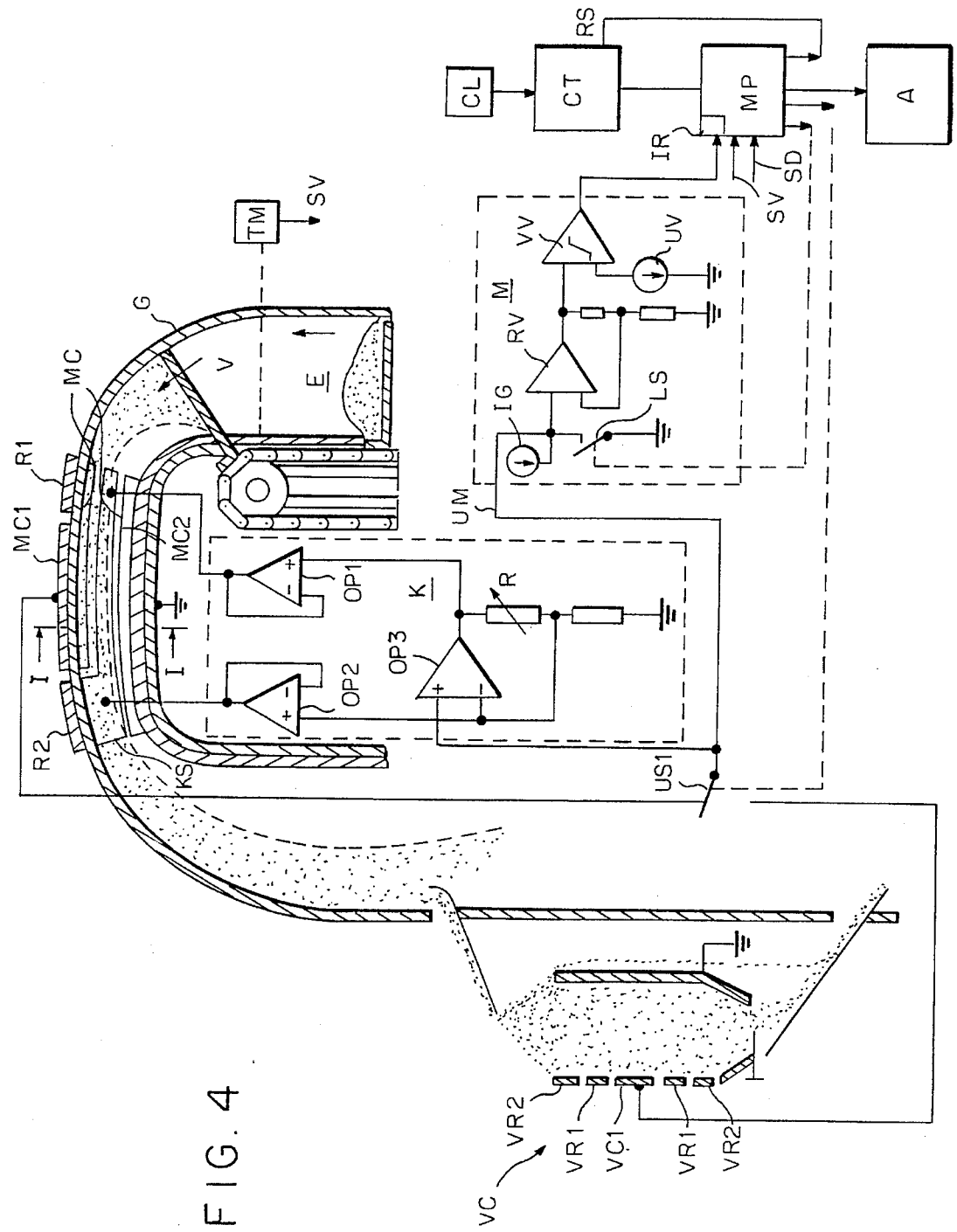
Figure 5:
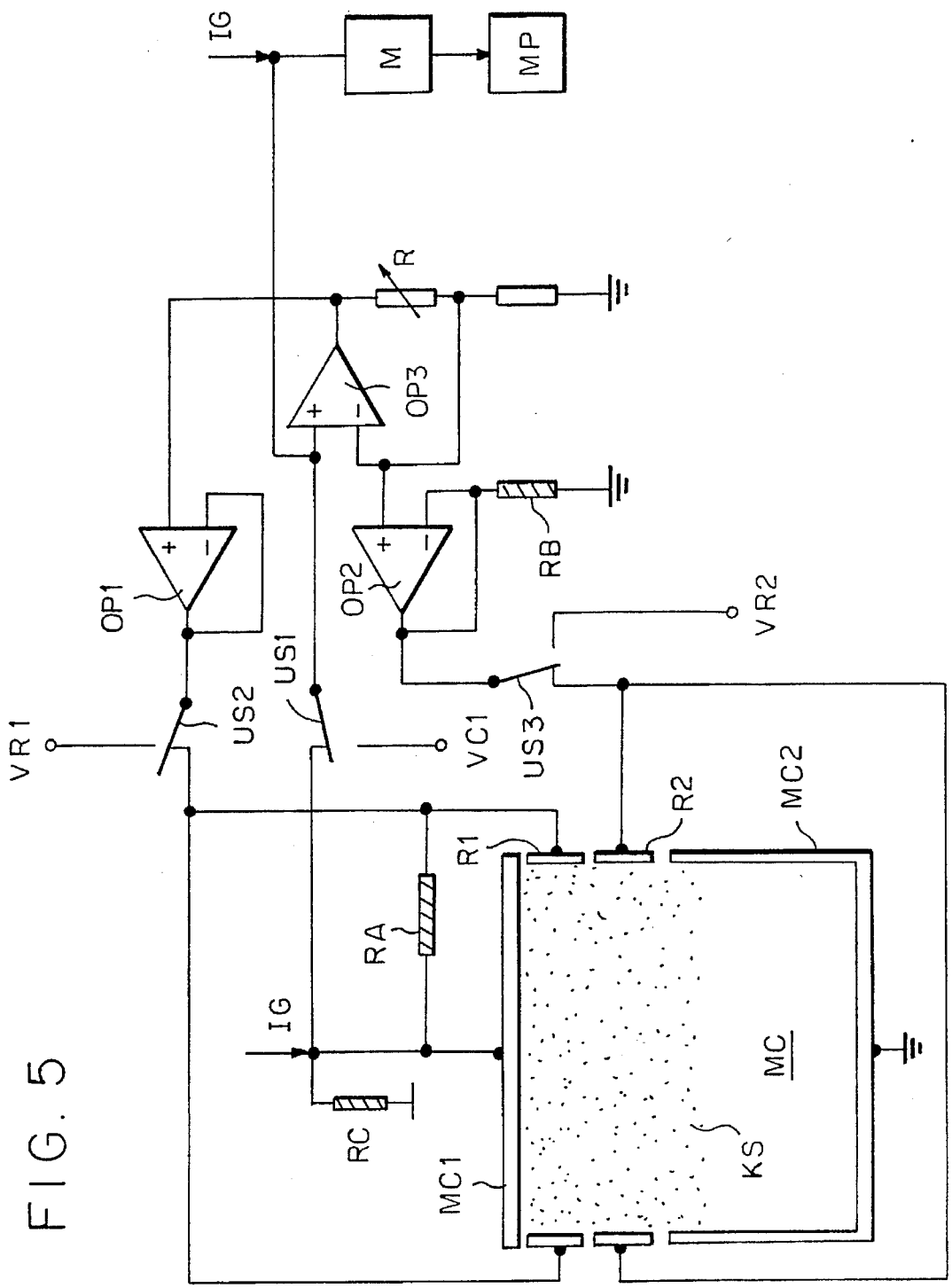

Exemplary embodiments are represented in the drawings and will be described in detail below. Shown are in:

FIG. 1, a vertical section through the measuring device with the measuring capacitor arrangement and measuring circuit, FIG. 2, a vertical section (II—II) through the conveyor conduit, FIG. 3, a magnified longitudinal section through the conveyor conduit with switchable electrodes, FIG. 4, a vertical section through the measuring device as in FIG. 1, but with an additional compensation circuit, FIG. 5, a vertical section (I—I) through the conveyor conduit with the measuring capacitor, protective electrodes and wiring.

FIG. 1 shows the upper portion of a grain elevator (E), whose conveyor shaft (G) causes a deflection of the grain flow (KS) ejected at the outlet into the first measuring capacitor (MC), so that the grain flow (KS) forms a stratified dielectric transversely to the path of the lines of electric flux. The capacitor (MC) is surrounded by a protective electrode (R1) which is supplied with the same voltage as the measuring plate (MC1). The backplate electrode (MC2) can be disposed to be insulated or grounded, depending on the measuring arrangement connected.

A comparison capacitor (VC) is disposed in the grain flow on the downstream side, which has such a small lower outlet that in continuous operation it is always filled to overflowing with grain. The measuring electrode (VC1) of this comparison capacitor (VC) is also enclosed by a protective ring electrode (VR1). The reference electrode of the comparison capacitor (VC) is electrically connected with the reference electrode (MC2) or they are both grounded. The two protective electrodes (R1, VR1) are electrically connected with each other, so that only one impedance converter is required as voltage tracking amplifier (NF).

A tachometer (TM) is disposed on the drive element of the elevator (E) which provides a measuring signal (SV) of the average grain flow velocity (V) to an evaluation device (MP).

The capacitance proportion which is converted in accordance with the mentioned functions is multiplied with the respective value of the velocity signal (SV) and a predetermined specific density value (SD), from which the mass flow value results, which is provided directly or via an integrator to a display device (A).

The signal (SV) of the velocity sensor corresponds to an average velocity of the grain, which increases with the distance from the turning axis in the course of the transition of the elevator blades from the lift movement into the rotating movement. Since the grains are driven outward by their centrifugal force, they interact by pushing in such a way that they assume an average velocity (V) of little spread width.

Since the functions of stratification and homogenization of the grain flow is only assured within a defined velocity range, the evaluation processor (MP) monitors the maintenance of this permissible velocity range by means of periodic comparisons of the velocity signal value (SV) with an upper and lower threshold value and issues an alarm report when it is upwardly or downwardly exceeded.

The density value (SD), which incidentally is moisture-dependent, can be determined from time to time and input into the evaluation processor (MP), or it is continuously determined gravimetrically by means of a weighing cell and is continuously supplied to the processor (MP).

A measuring circuit (M) of a simple design provides a digitalization of the capacitance values of the two capacitors (MC, VC).

The measuring electrodes (MC1, VC1) of the two capacitors are selectively connected, controlled via a reversing switch (US1), with the input of the measuring circuit (M). It is supplied from a current source (IG) and leads to a ramp signal amplifier (RV), whose output leads to a comparator (VV), whose other input is supplied with a comparison voltage (UV).

On the input side, the evaluation processor (MP) is connected with the output of a counter (CT), whose counter input is continuously charged with clock signals (CL). Each time the ramp voltage corresponds to the comparison voltage (UV), the output of the comparator (VV) controls an interrupt input (IR) of the evaluation processor (MP). As a result, the latter controls via a quenching transistor (LS) a discharge of the measuring capacitance, the placement of the reversing switch (US1) into the respectively other position, the transfer of the contents of the counter into an interior memory and a set-back (RS) of the counter (CT). In the same way, when the comparison voltage (UV) is next reached, a further counter setting is transferred to another internal memory, upon which both respective counter settings obtained, which directly correspond to the two capacitance values, are placed into proportion. The calculated proportional value is then further processed in accordance with the function of the stratified dielectric and is then linked with the velocity value (SV) and a density value (SD), so that the mass flow respectively results, which is provided directly or in an integrated manner to an output device (A).

In accordance with the invention, the protective electrode (R1) is turned down on the lateral walls of the conveyor shaft (G), so that the lines of electric flux of the measuring electrode (MC1) extend approximately parallel in relation to the backplate electrode (MC2) and a calculable dependency of the grain layer height is provided in this way. With very large grain throughput it is provided to connect the protective electrode (R1) with a further partial electrode area (R2) extending in the direction towards the capacitor plate (MC2) located on the opposite side in order to obtain as parallel as possible a field formation in these cases, too. With a low state of the grain flow (KS), the partial electrode (R2) is advantageously connected with the adjoining backplate electrode (MC2) via a reversing switch (US). This backplate electrode is also pulled up past the horizontal area to the lateral walls and partially covers them.

The reversing switch (US) which switches over the second partial electrode (R2) is controlled by the evaluation processor (MP). Switch-over suitably takes place when the evaluation shows that a predetermined threshold value of the relationship between the capacitances of the two capacitors (MC, VC) has been exceeded. This threshold relationship has been selected such that switch-over takes place before the fill level reaches the area of the first protective electrode (R1).

Since a certain capacitance change of the flow rate measuring capacitor (MC) occurs with the switch-over of the partial electrode (R2), it has been provided in an advantageous manner to equip the comparison capacitor (VC), in addition to a protective electrode (VR1), also with a partial electrode (VR2) which is disposed between the protective electrode (VR1) and the enclosed measuring electrode (VC1).

The capacitance conditions of this partial electrode (VR2) of the comparison capacitor (VC) are selected such that they correspond to the capacitance conditions during the switch-over of the partial electrode (R2) of the measuring capacitor (VC). So that both capacitances (MC, VC) are independent of the switch-over, a further reversing switch (USR) is provided for the partial electrode (VR2) of the comparison capacitor and is connected analogously to the first reversing switch (US) and controlled parallel with it.

In place of the disposition of the second reversing switch (USR) it is possible to compensate the capacitance change by means of an appropriate calculated consideration during processing of the measured values.

A measured section is constructed in the elevator head in FIG. 2, which shows a section (II—II) on a changed scale, in which under the influence of centrifugal forces a stratification of the grain flow (KS1, KS2), whose layer height is proportional to the throughput, is noted on the exterior wall. The grain layer generated in this way, together with the adjoining layer of air, forms the stratified dielectric of a plate capacitor consisting of a measuring electrode (MC1) provided with a protective ring (R1) and of the backplate electrode (MC2) connected to ground. In this arrangement and with a respectively suitable geometrical dimensioning of the width of the protective ring electrode and the measuring electrode (MC1), a largely homogeneous electrical field is formed in front of the latter, which assures a detection of the layer height of the grain flow by means of a high-grade defined, approximately linear electrical measuring technique. Assuming that the electrical field extends indefinitely transversely to the direction of flow of the grain, i.e. that no electrode walls would cause a lateral potential limitation, the inescapable inhomogeneities of the field are only formed in front of the protective electrode (R1). In this way they can be eliminated from the capacitance detection without problems in a very simple manner by voltage tracking by means of the impedance converter (NF). In an advantageous manner it is provided that by means of the impedance converter (NF) the protective ring electrode (R1) continuously tracks the measuring voltage (UM) present at the measuring capacitor (MC1) exactly, except for an error voltage of maximally 1 µV.

The different heights (h1, h2) with a low grain flow (KS1) and a high grain flow (KS2) are indicated in the cross section. The formulas of the stratified dielectric relate to the respectively given height of the grain flow and the total height (H) between the capacitor plates (MC1, MC2). The reversing switch (US) switches the partial electrode (R2) respectively to the second capacitor plate (MC2) when the layer height is less than a threshold value which corresponds, for example, to the illustrated low grain flow height (h1). It fills the protective electrode (R1) disposed on the lateral wall to approximately 80%. The useful signal, the measuring voltage (UM), is picked up directly upstream of the first capacitor plate and passed to the measurement processing circuit (M) and from there to the evaluation processor (MP).

Since the lines of electrical flux are strictly parallel to the displacement current density lines, a relative dielectric constant $Epsilon_{rK}$ in accordance with the formulas for stratified dielectrics results for the two layers of the dielectric of the grain layer thickness (h1) and the air layer thickness (H–h1) and the associated averaged electrical field strengths in accordance with the equation $$\frac{E_H - h1}{E_{h1}} = \frac{Epsilon_K}{Epsilon_L} \approx Epsilon_{rK}$$

wherein the subscripts K and L are used for grain or air. A capacitive determination of the grain layer height (h1) is easily possible with this, since it is approximately determined exclusively from the relative dielectric constant of the grains.

The comparison capacitor (VC) can also be disposed in a reservoir (not shown) which must be periodically emptied, instead of in a continuous partial mass flow, provided the bulk material is the same in respect to its capacitive properties over an appropriately long period of time. With an arrangement of this type it is necessary to determine by means of a prior test of the capacitance measuring value whether the measuring capacitor is already filled, i.e. whether the reservoir is already partially filled in respect to the position of the flow rate measurement capacitor (MC), since until this time the capacitor has a fixed known starting capacitance which is determined by the air portion of the dielectric. In the course of the capacitance comparison of the measuring capacitor (MC) with the stratified dielectric, first, as long as the comparison capacitor (VC) has not yet been filled, the mass flow for the given bulk material is approximately determined, taking into consideration empirical calibrating values of the capacitive properties. As soon as the measuring capacitor (MC) in the reservoir has been filled and the actual material-specific comparison value of the capacitance is determined, which can be respectively determined by a comparison of the capacitance value in relation to is approximate constancy over time and when a predetermined capacitance threshold value is exceeded, the automatic consideration of the capacitive material properties takes place. Furthermore, the previously measured and empirically approximately determined measuring values which had been stored in the interim are corrected in accordance with the measured capacitive material correction value.

The measurement of the capacitance of the completely filled comparison capacitor (VC) is furthermore advantageously used to determine the respective moisture of the measured material in accordance with a calibrating function which provides the connection between the moisture content of the bulk material as a function of the measured capacitance, and to show it by means of a display or a printout.

The functional connection of the dielectric constant Epsilon as a function of the moisture content for wheat is recited in Kutzbach: Lehrbuch der Agrartechnik Bd. 1, Allgemeine Grundlagen, Ackerschlepper, Fördertechnik [Textbook on Agricultural Technology, Vol. 1, General Basics, Farming Tractors, Conveyor Technology]. For other materials it is possible to determine appropriate functions of the capacitance connection of the measuring capacitor from the material properties or material compositions. The conversion of the measured capacitance values can be easily performed by means of access to tables and possibly an interpolation between the stored values. In this way it is possible by means of the function shown to determine the moisture from the capacitance relationships, which are determined from the capacitance of the respectively filled capacitor and a one-time measurement of the capacity with completely dry material of the same type.

FIG. 3 shows a further advantageous embodiment of the invention, which can also be combined with the embodiments of FIGS. 1 and 2. In this arrangement the capacitor plate (MC1) on the side of the grain flow is selectively connected via reversing switches (UD1, UD2) with an electrode section (R3) or (R4), one of which is downstream and the other upstream of the capacitor plate (MC1). The entire arrangement of the plate and the two partial electrodes is enclosed by a protective electrode (R1), which also extends to the lateral walls of the conveyor shaft. In case of dry grain (FT), the conveyed material moves in the conveyor shaft over an extended path along the curved exterior wall. Moist grain (FF), however, because of its increased friction moves only over a portion of the exterior wall in the vicinity of the wall and then moves away from it in a shortened arc.

So that measurement takes respectively place in as homogeneous as possible a grain flow, the downstream partial electrode (R3) is switched together with the capacitor plate (MC1) if there is dry grain (FT). The upstream partial electrode (R4) is switched in correspondingly when there is moist grain (FF). The respective partial electrode (R3, R4) not used together with the measuring electrode is then respectively connected with the protective electrode (R1) via its reversing switch (UD1, UD2). The parallel control of the two reversing switches (UD1, UD2) is performed via the evaluation processor (MP) by means of the employment of the moisture measurement signal which, as already described, is obtained in particular from the measured values of the comparison capacitor (VC). This takes place in that every time a threshold value of the moisture content set for the respective grain type is exceeded, the partial electrode (R3) located on the upstream slide of the capacitor plate (MC1) is switched in, and the other partial electrode (R4) is connected to the protective electrode (R1). The two partial electrodes (R3, R4) are suitably embodied such that the capacitance of the respective capacitor plate formed with them is respectively the same.

A compensating circuit (K) is illustrated in FIGS. 4 and 5, by means of which the two protective electrodes (R1, R2) are tracking the voltage of the measuring electrode (MC1), wherein the protective electrodes (R1, R2) are wired in such a way, that separately controllable they compensate leakage currents which flow away from the measuring electrode (MC1) or to it. When using this compensation circuit (K), an insulating coating on the electrodes is superfluous.

These leakage currents occur in connection with a continuous water film extending over the electrode surfaces. They flow between the measuring electrode (MC1) and the protective electrode(s), between the measuring electrode (MC1) and the backplate electrode (MC2) and between the protective electrode(s) and the backplate electrode (MC2). The capacitance measurement is distorted by these ohmic conductor portions.

The respective replacement resistors (RA, RB, RC) over which the leakage currents flow have been drawn in FIG. 5 for clarification. A portion of the current provided by the current source (IG) is lost through these resistors. Respectively one impedance converter (OP1, OP2) is associated with each of the two protective electrodes (R1, R2). These impedance converters (OP1, OP2) are controlled by an amplifier (OP3) which is associated with the measuring electrode (MC1) and is supplied by the measuring voltage (UM) on the input side.

The leakage current flowing between the measuring electrode (MC1) and the protective electrodes (R1, R2) is mainly compensated in this way. The leakage current between the measuring electrode (MC1) and the backplate electrode (MC2), as well as between the protective electrodes (R1, R2) and the backplate electrode (MC2) is mainly compensated via the impedance converter (OP1) and the protective electrode (R1). The amplification factor of the amplifier (OP3) and the distribution ratio of the compensating currents to the respective protective electrodes (R1, R2) can be set to the optimal value by means of a variable resistor (R). In one embodiment the impedance converters (OP1, OP2) and the amplifier (OP3) are constituted by operational amplifiers.

The comparison capacitor (VC) also has two protective electrodes (VR1, VR2) which enclose the measuring electrode (VC1). The measuring electrode (VC1) and the protective electrodes (VR1, VR2) can be connected via reversing switches (US1, US2, US3) with the compensating circuit (K), so that only one common compensating circuit (K) is required for the mass flow measuring capacitor (MC) and the comparison capacitor (VC). For reasons of clarity, only the reversing switch (US1) is shown in FIG. 1.

The reversing switches (US1, US2, US3) are preferably MOSFET transistors or relay contacts.

The comparison capacitor (VC) can advantageously be designed as a cylinder capacitor, because of which only small edge area with inhomogeneous field distribution occur.

This device can be employed in combines, straw, grass or corn choppers and in hay, straw or grass collectors.

Further than that, such a device can be employed in all cases where it is necessary to measure the capacitance of a stratified dielectric with a comparatively high moisture content.

We claim:

1. In a device for measuring a mass flow which is deflected at the outlet of an elevator (E) at a conveyor shaft wall (G), in particular of a harvester, such that it forms a stratified dielectric with a homogeneous speed in a flow rate measuring capacitor (MC) disposed there, a capacitance of the capacitor being a function of the fill level and being continuously measured, wherein a first capacitor plate (MC1) of the capacitor is disposed at a mass flow front side and a second capacitor plate (MC2) of the capacitor is disposed at a distance from the mass flow, and wherein the first capacitor plate (MC1) is bordered by a first protective electrode (R1) which is kept at the same potential with the first capacitor plate (MC1) enclosed by the first protective electrode by an impedance transformer means for keeping at a same potential, and wherein the second capacitor plate (MC2) is formed by a portion of the conveyor shaft wall located opposite the first capacitor plate (MC1) and by lateral areas of the conveyor shaft wall; the improvement comprising:

in addition to the first protective electrode (R1), the device includes at least one partial second protective electrode (R2) which by a switching means is held at a different potential of the first protective electrode (R1) and the first protective electrode (R1) extends at least partially perpendicular to the front side on the side walls of the conveyor shaft between the two capacitor plates (MC1, MC2) over at least a partial height (h1, h2) of the mass flow (KS).

2. The improvement according to claim 1, wherein the partial second protective electrode (R2) is disposed between the second capacitor plate (MC2) and the first protective electrode (R1) and the partial second protective electrode (R2) is controllable by a reversing switch means (US) for selectively connecting the partial second protective electrode with the first protective electrode (R1) and with the second capacitor plate (MC2).

3. The improvement according to claim 2, characterized in that the width of the second partial electrode (R2) approximately corresponds to the difference in the height (h1, h2) of the mass flow at a low and at a high mass flow.

4. The improvement according to claim 1, characterized in that the partial second protective electrodes (R3, R4) are disposed on both sides of the first capacitor plate (MC1) between the first capacitor plate and the first protective electrode (R1) on the front wall of the conveyor shaft, as viewed in the conveying direction, which partial second protective electrodes are selectively connected via further controllable reversing switches (UD1, UD2) respectively with the protective electrode (R1) or with the first capacitor plate (MC1).

5. The improvement according to claim 4, characterized in that the two partial second protective electrodes (R3, R4) have the same capacitances and that the further two reversing switches (UD1, UD2) are controllably switched as double-pole reversing switches in such a way that a respective one or another of the partial second protective electrodes (R3, R4) is alternatingly connected with the first protective electrode (R1).

6. The improvement according to claim 5, characterized in that the reversing switches (US, UD1, UD2) are MOSFET transistors or relay contacts and that they are controlled via an evaluation processor (MP) and that the flow rate measuring capacitor (MC) is connected via a measuring circuit (M) with the evaluation processor (MP) and that the input of the measuring circuit (M) is furthermore connected with a compensating capacitor (VC) which is continuously filled with a partial mass flow, with whose compensating capacitance the measuring circuit (M) is placed in a relationship by the measuring capacitor capacitance, which forwards this capacitance relationship value to the evaluation processor (MP) which, respectively as a function of a predetermined threshold value being exceeded, controls the reversing switch (US) by means of the relationship value in such a way, that the partial second protective electrode (R2) is connected with the first protective electrode (R1).

7. The improvement according to claim 6, characterized in that a capacitance value of the comparison capacitor (VC) is provided to the evaluation processor (MP) and that the latter, each time a predetermined comparison value has been exceeded, controls the further reversing switches (UD1, UD2) in such a way that the partial second protective electrode (R4) located upstream in the mass flow is connected with the first capacitor plate (MC1).

8. A device in accordance with claim 1, characterized in that the first protective electrode (R1) is linked via a first impedance convertor (OP1) to the potential of the first capacitor plate (MC1) and the partial second protective electrode (R2) is linked via a second impedance convertor (OP2) to the potential of the first capacitor plate (MC1) by means of an electrode leakage current compensating circuit (K) consisting of an amplifier (OP3) whose input is connected to the capacitor plate (MC1) and the output of which is connected to the inputs of the said impedance convertors (OP1, OP2) in a leakage current compensating ratio.

9. The improvement according to claim 8, characterized in that the amplification factor of the amplifier (OP3) and the ratio of the leakage compensating currents to the respective first and second protective electrodes (R1, R2) can be set to the optimal value by means of a variable resistor (R) at the output of the amplifier (OP3).

10. The improvement according to claim 8, characterized in that the impedance convertors (OP1, OP2) and the amplifier (OP3) are constituted by operational amplifiers.

11. The improvement according to claim 1, characterized in that the comparison capacitor (VC) has at least two protective electrodes (VR1, VR2) and that the comparison capacitor (VC) can be connected with the compensating circuit (K) via reversing switches (US1, US2, US3).

12. The improvement according to claim 1, characterized in that the protective electrodes (R1, R2) extend at least partially on the lateral walls of the conveyor shaft between the capacitor plates (MC1, MC2).

13. The improvement according to claim 1, characterized in that the partial electrode (R2) is used as a second separate protective electrode, wherein the protective electrodes (R1, R2) and the measuring electrode (MC1) are wired by means of a compensating circuit (K) in such a way that the protective electrodes (R1, R2) track the potential of the measuring electrode (MC1) and in the process leakage currents are compensated by means of the compensating circuit (K) and the protective electrodes (R1, R2).

14. The improvement according to claim 2, characterized in that the reversing switches (US, UD1, UD2) are MOSFET transistors or relay contacts and that they are controlled via an evaluation processor (MP) and that the flow rate measuring capacitor (MC) is connected via a measuring circuit (M) with the evaluation processor (MP) and that the input of the measuring circuit (M) is furthermore connected with a compensating capacitor (VC) which is continuously filled with a partial mass flow, with whose compensating capacitance the measuring circuit (M) is placed in a relationship by the measuring capacitor capacitance, which forwards this capacitance relationship value to the evaluation processor (MP) which, respectively as a function of a predetermined threshold value being exceeded, controls the reversing switch (US) by means of the relationship value in such a way, that the second partial electrode (R2) is connected with the protective electrode (R1).

15. The improvement according to claim 1, characterized in that partial electrodes (R3, R4) are disposed on both sides of the first capacitor plate (MC1) between it and the protective electrode (R1) on the front wall of the conveyor shaft, viewed in the conveying direction, which are selectively connected via further controllable reversing switches (UD1, UD2) respectively with the protective electrode (R1) or with the first capacitor plate (MC1).

16. The improvement according to claim 1, characterized in that at least one second partial electrode (R2) is disposed between the second capacitor plate (MC2) and the first partial protective electrode (R1) which, controlled by means of a reversing switch (US), can be selectively connected with the first partial protective electrode (R1) to act as a further partial protective electrode, or with the second capacitor plate (MC2) to act as a part thereof.

17. The improvement according to claim 10, characterized in that the partial second protective electrodes (R2) extend at least partially on the side walls of the conveyor shaft between the capacitor plates (MC1, MC2).

18. A device in accordance with claim 6 characterized in that the first protective electrode (R1) is linked via a first impedance converter (OP1) to the potential of the first capacitor plate (MC1) and the partial second protective electrode (R2) is linked via a second impedance converter (OP2) to the potential of the first capacitor plate (MC1) by means of an electrode leakage current compensating circuit (K) consisting of an amplifier (OP3) whose input is connected to the capacitor plate (MC1) and the output of which is connected to the inputs of the said impedance converters (OP1, OP2) in a leakage current compensating ratio, further the input of the amplifier (OP3) of the leakage current compensating circuit (K) as well as the outputs of the impedance converters (OP1, OP2) are in parallel mutually switchable by means of related reversing switches (US1, US2, US3) respectively to a capacitor electrode (VC1) of the comparison capacitor (VC) and first and second protective electrodes (VR1, VR2) arranged with the said capacitor electrode (VC1).

* * * * *